US00PP23917P2

(12) United States Plant Patent
Sakaue

(10) Patent No.: US PP23,917 P2
(45) Date of Patent: Sep. 24, 2013

(54) ***CAMPSIS* PLANT NAMED 'TAKARAZUKA FRESA'**

(50) Latin Name: *Campsis×tagliabuana*
Varietal Denomination: Takarazuka Fresa

(76) Inventor: Koichi Sakaue, Takarazuka (JP)

( * ) Notice: Subject to any disclaimer, the term of this patent is extended or adjusted under 35 U.S.C. 154(b) by 100 days.

(21) Appl. No.: 13/385,119

(22) Filed: Feb. 2, 2012

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Penny J. Aguirre

(57) ABSTRACT

A new cultivar of *Campsis* hybrid, 'Takarazuka Fresa', characterized by its dark green, clean foliage, its flowers that are red in color with throat black veining, and its compact, upright and vining plant habit.

1 Drawing Sheet

Botanical classification: *Campsis×tagliabuana*.
Variety denomination: 'Takarazuka Fresa'.

CROSS REFERENCE TO RELATED APPLICATIONS

This application is co-pending with U.S. Plant Patent Applications related to plants derived from the same breeding program. The Applications are entitled; *Campsis* Plant Named 'Takarazuka Zujin' (U.S. Plant patent application Ser. No. 13/385,116) and *Campsis* Plant Named 'Takarazuka Yellow' (U.S. Plant patent application Ser. No. 13/385,122).

BACKGROUND OF THE INVENTION

The present invention relates to a new and distinct cultivar of *Campsis×tagliabuana* (*C. grandiflora×C. radicans*) and will be referred to hereafter by its cultivar name, 'Takarazuka Fresa'. 'Takarazuka Fresa' is a new cultivar of perennial vine for use as a landscape plant.

'Takarazuka Fresa' originated as a seedling that arose from seed planted from an open pollination of unnamed plants of *Campsis×tagliabuana* from the Inventor's breeding line in Shizuoka Prefecture Takarazuka, Japan in 1995. The parents are therefore unknown. The new *Campsis* was selected as a single unique plant in 2000.

Asexual reproduction of the new cultivar was first accomplished by the Inventor using softwood stem cuttings in 2008 in Takarazuka, Japan. The characteristics of the new cultivar have been determined to be stable and are reproduced true to type in successive generations.

SUMMARY OF THE INVENTION

The following traits have been repeatedly observed and represent the characteristics of the new cultivar as grown outdoors in trial beds and in containers in Takarazuka, Japan. These attributes in combination distinguish 'Takarazuka Fresa' as a unique cultivar *Campsis*.

1. 'Takarazuka Fresa' exhibits dark green, clean foliage.
2. 'Takarazuka Fresa' exhibits flowers that are red in color with black veining on throat.

3. 'Takarazuka Fresa' exhibits a compact, upright vining plant habit.

'Takarazuka Fresa' can be most closely compared to cultivars derived from the same breeding program; 'Takarazuka Zujin' and 'Takarazuka Yellow'. 'Takarazuka Zujin' differs from 'Takarazuka Fresa' in having flowers that are orange-red in color, in having an even more compact plant habit and in commencing bloom earlier in the season. 'Takarazuka Yellow' differs from 'Takarazuka Fresa' in having flowers that are larger and peach orange to yellow in color. 'Takarazuka Fresa' can also be compared to the cultivars 'RUTCAM' (U.S. Plant Pat. No. 19,415) and 'HOMR' (U.S. Plant Pat. No. 18,394). 'RUTCAM' differs from 'Takarazuka Fresa' in having flowers that are deeper red in color, in having a less compact plant habit and in having pubescent leaves. 'HOMR' differs from 'Takarazuka Fresa' in having flowers that are pinkish red in color and in having pubescent leaves and stems.

BRIEF DESCRIPTION OF THE DRAWING

The accompanying colored photograph illustrates the overall appearance and distinct characteristics of a one year-old plant of the new *Campsis* as grown outdoors in a one-gallon container in Takarazuka, Japan. The photograph in FIG. 1 provides a close-up view of the flowers, flower buds, and a young leaf of 'Takarazuka Fresa'. The colors in the photographs are as close as possible with the digital photography techniques utilized and the color values cited in the detailed botanical description accurately describe the colors of the new *Campsis*.

DETAILED BOTANICAL DESCRIPTION

The following is a detailed description of one year-old plants of the new *Campsis* as grown outdoors in one-gallon containers in Takarazuka, Japan. The phenotype of the new cultivar may vary with variations in environmental, climatic, and cultural conditions, as it has not been tested under all possible environmental conditions. The color determination is in accordance with The 2007 R.H.S. Colour Chart of the Royal Horticultural Society, London, England, except where general color terms of ordinary dictionary significance are used.

General description:

*Blooming period*.—Blooms from May through July in Japan.

*Plant type*.—Perennial vine, deciduous in U.S.D.A. Zone 5.

*Plant habit*.—Compact, upright vine.

*Height and spread*.—Reaches about 50 cm in height and 40 cm width in one year.

*Hardiness*.—At least in U.S.D.A. Zone 5.

*Diseases resistance*.—No disease resistance or susceptibility has been observed.

*Root description*.—Fibrous.

*Propagation*.—Softwood stem cuttings.

*Growth rate*.—Vigorous.

*Roots*.—Fibrous.

Stem description:

*Shape*.—Round.

*Stem color*.—Young growth; 144A, mature wood 200D.

*Stem size*.—Main stems; to 50 cm in length and an average of 2.8 mm in width, lateral branches; with an average of 20 cm cm in length and 2 mm in width.

*Stem surface*.—Glabrous.

*Internode length*.—Average of 5 cm.

*Branching*.—5 lateral branches.

Foliage description:

*Leaf division*.—Pinnately compound with 7 to 10 leaflets.

*Leaf arrangement*.—Opposite.

*Leaf attachment*.—Petiolate.

*Leaf size*.—Range from 15 to 35 cm in length and 4 to 20 cm in width.

*Leaflet size*.—Range from 2 to 12 cm in length and 1 to 5 cm in width.

*Leaflet shape*.—Elliptic to ovate-oblong.

*Leaflet base*.—Cuneate.

*Leaflet apex*.—Acuminate to long acuminate.

*Leaflet venation*.—Pinnate, not prominent, color on upper surface 144C to 144D on upper and lower surface.

*Leaflet margins*.—Irregularly serrated to crenated.

*Leaflet arrangement*.—Odd pinnate.

*Leaflet attachment*.—Winged petiolules.

*Leaflet aspect*.—Slightly concave from midrib.

*Leaflet surface*.—Glabrous, smooth and moderately glossy on upper surface and glabrous, smooth and slightly glossy on lower surface.

*Leaflet color*.—New growth upper surface and lower surface; 144B, mature leaves upper surface; 137C, mature leaves lower surface; 137D.

*Petioles*.—Range from 4 to 7 cm and an average of 2 mm in length, 137B in color, sparsely pubescent surface.

*Petiolules*.—Ranges from 0.5 cm and 1 cm in length and an average of 2 mm in width, winged with base swollen, 137B in color with a spot of 178B at base on young leaves, glabrous surface.

*Rachis*.—Ranges from 7 to 11 cm in length (including petiole) and an average of 2 mm in width, 137B in color, sparsely pubescent surface.

*Stipules*.—Not present.

Inflorescence description:

*Inflorescence type*.—Terminal cluster, blooms on current year's growth.

*Inflorescence size*.—An average of 20 cm in depth and width.

*Flower buds*.—Elliptic in shape, about 2 cm in length and 1.5 cm in width, color is 40A suffused with 42A.

*Flower fragrance*.—None.

*Lastingness of flowers*.—Individual flowers last about 5 to 7 days.

*Flower quantity*.—5 to 15 flowers per inflorescence.

*Flower type*.—Tubular.

*Flower aspect*.—Upright to outward.

*Flower size*.—Average of 8 cm in length, 5 cm in diameter at apex and 5 mm in diameter at base.

*Peduncles*.—Average of 10 cm in length and 3 mm in diameter, 144A in color, glabrous surface, round in shape, held upright to about a 30° angle to stem (0% equal to vertical).

*Pedicels*.—Average of 1 cm in length and 1 mm in diameter, round in shape, 144A in color, glabrous surface.

*Calyx form*.—Campanulate with base fused.

*Sepals*.—5, lanceolate in shape, apiculate apex, fused base, an average of 2.5 cm in length and 5 mm in width, entire margin, color of upper and lower surface 40A and suffused with 40B, glabrous and satiny surface.

*Corolla*.—Tubular with apex flared, tube is an average of 6 cm in length and 1 cm in width.

*Petals*.—5, flabellate in shape with lobes rounded, upper and lower surface is smooth, margin entire to slightly notched, fused base, round apex, about 8 cm in length with lobe portion about 2 cm in width and depth, color of upper and lower surface of lobe portion; 40A with throat of inner surface (tube portion) a blend of 40A and 200A with ridges of 200A, outer surface of tube portion; a blend of 40A and 26B.

Reproductive organs:

*Gynoecium*.—Pistil; 1, about 5.5 mm in length, 18B in color.

*Androcoecium*.—Stamens; 4, anthers; narrowly elliptic in shape, an average of 3 cm in length, 20A in color, pollen; moderate in quantity and 18B in color.

*Seed*.—Not observed.

It is claimed:

1. A new and distinct cultivar of *Campsis* plant named 'Takarazuka Fresa' as herein illustrated and described.

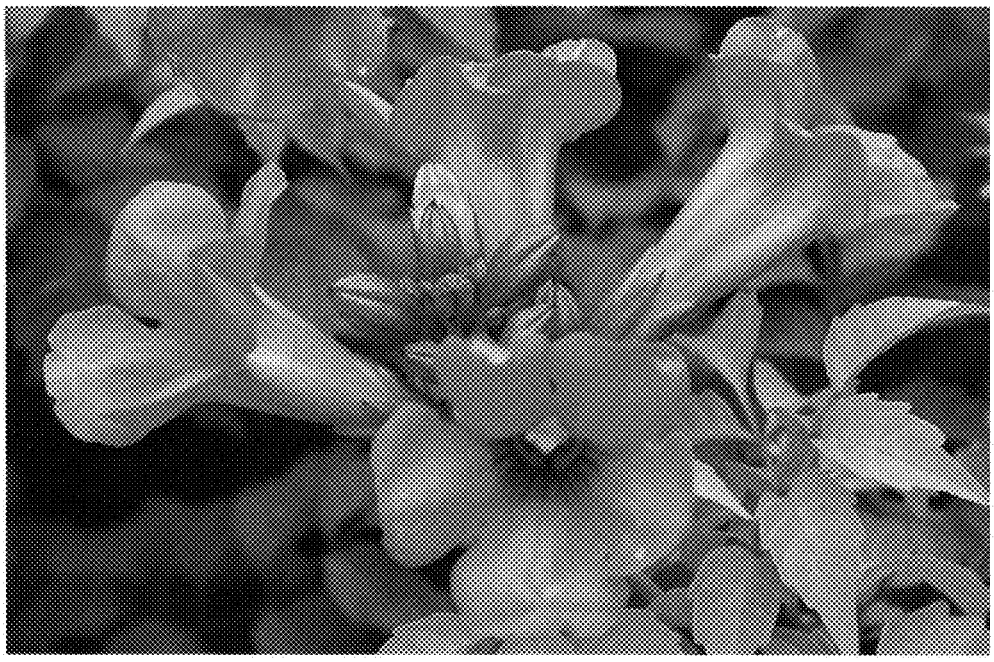

* * * * *